US012590938B2

(12) United States Patent
Wu et al.

(10) Patent No.: US 12,590,938 B2
(45) Date of Patent: Mar. 31, 2026

(54) POLLUTANT DETECTION EQUIPMENT FOR ENVIRONMENTAL SCIENCE

(71) Applicant: BEIJING NORMAL UNIVERSITY AT ZHUHAI, Zhuhai (CN)

(72) Inventors: Zihao Wu, Zhuhai (CN); Shengrui Wang, Zhuhai (CN); Xinfeng Zhao, Zhuhai (CN); Wenhui Gan, Zhuhai (CN); Xinrui Cai, Zhuhai (CN); Xuanzhi Ma, Zhuhai (CN)

(73) Assignee: BEIJING NORMAL UNIVERSITY AT ZHUHAI, Zhuhai (CN)

( * ) Notice: Subject to any disclaimer, the term of this patent is extended or adjusted under 35 U.S.C. 154(b) by 383 days.

(21) Appl. No.: 18/518,125

(22) Filed: Nov. 22, 2023

(65) Prior Publication Data

US 2024/0175856 A1     May 30, 2024

(30) Foreign Application Priority Data

Nov. 25, 2022     (CN) .......................... 202211487284.2

(51) Int. Cl.
G01N 33/18          (2006.01)
G01N 1/14           (2006.01)
(52) U.S. Cl.
CPC ............... G01N 33/18 (2013.01); G01N 1/14 (2013.01)

(58) Field of Classification Search
CPC ...... G01N 33/18; G01N 1/14; G01N 33/1826; Y02A 20/20
See application file for complete search history.

(56) References Cited

FOREIGN PATENT DOCUMENTS

| CN | 106771025 A | * | 5/2017 | ......... G01N 33/1806 |
| CN | 115032357 A | * | 9/2022 | ............. A01D 44/00 |

* cited by examiner

*Primary Examiner* — Timothy P Graves
(74) *Attorney, Agent, or Firm* — Keller Preece PLLC

(57) ABSTRACT

A new pollutant detection equipment for environmental science is provided. The water is pumped in through the pumping seat. After being sensed through the sensor heads inside, the data is analyzed by detection machine, which output the result to the data panel to detect the water resources. During detecting, the water is pumped in through the water inlet pipe. After the water flows onto the separation block, the water is guided by the guide block and then rapidly rushes into the separation ring. The driven frame is driven to rotate by the incoming water. If there are a lot of root systems of duckweed in the water, the root systems can be concentrated and cut up through the driven frame, and then they continue to move backwards and cut for a second time.

8 Claims, 7 Drawing Sheets

POLLUTANT DETECTION EQUIPMENT FOR ENVIRONMENTAL SCIENCE

CROSS-REFERENCE TO RELATED APPLICATION

This patent application claims the benefit and priority of Chinese Patent Application No. 202211487284.2 filed with the China National Intellectual Property Administration on Nov. 25, 2022, the disclosure of which is incorporated by reference herein in its entirety as part of the present application.

TECHNICAL FIELD

The present disclosure relates to the field of environmental science, in particular to a new pollutant detection equipment for environmental science.

BACKGROUND

New pollutants refer to a type of pollutants which are produced by human activities and exist clearly at present, but there are no relevant standards or clear regulations to restrict them, so that the pollutants are harmful to life and ecological environment. At present, there are mainly four types of new pollutants concerned all over the world: persistent organic pollutants (POPs), endocrine disrupting chemicals (EDCs), antibiotics and microplastics. Convenient and efficient detection of new pollutants is an important prerequisite for accelerating the treatment of new pollutants. Existing new pollutant detection equipment cannot realize on-site detection, especially when a water area full of duckweed is detected on site for endocrine disrupters. Because the root system of duckweed is well-developed and penetrates into the water, when a water quality detection equipment is used for on-site detection, the root system of duckweed is easily pumped in and entangled in the pumping structure during the pumping process, so that the pumping structure is easily jammed and blocked, the water cannot be pumped in smoothly, and the accurate detection result is difficult to obtain.

SUMMARY

Because the root systems of duckweed are well-developed and penetrate into the water, when a water area full of duckweed is detected by a water quality detection equipment on site, the root systems of duckweed are easily pumped in and entangled in the pumping structure during the pumping process, so that the pumping structure is easily jammed and blocked, the water cannot be pumped in smoothly, and the accurate detection result is difficult to obtain. Aiming at the above problems, the present disclosure provides a new pollutant detection equipment for environmental science.

In order to achieve the above purpose, the following technical solution is proposed by the present disclosure. The new pollutant detection equipment for environmental science structurally includes a detection machine, a carrying handle, a data panel and a pumping seat. A top surface of the detection machine is connected with a bottom surface of the carrying handle through welding. A top surface of the pumping seat is connected with a bottom surface of the detection machine through embedding. The data panel is embedded in a right side of the detection machine. The pumping seat includes a connecting block, a pumping pipe, a discharge pipe and sensor heads. A top surface of the connecting block is connected with the bottom surface of the detection machine through embedding. The pumping pipe is embedded in an interior of the connecting block. A right end of the discharge pipe and a left end of the pumping pipe are in communication with each other and movably engaged. Each of the sensor heads are embedded in a top surface of the pumping pipe. The discharge pipe is a tubular structure including two plates with a triangular cross section, and the two plates are pivotably connected to upper and lower portions of the left end of the discharge pipe through a hinge shaft.

Furthermore, the pumping pipe includes a water inlet pipe, a guide pipe and buffer pipes. A left end of the water inlet pipe and a right end of the guide pipe are in communication with each other and connected through embedding. Both ends of each of the buffer pipes and a middle section of the guide pipe are in communication with each other and connected through electric welding. Each of the sensor heads are embedded in a top surface of the buffer pipe. The buffer pipe is of a spherical tube structure with a smooth inner wall.

Furthermore, the water inlet pipe includes an expansion pipe, a separation block, a concentration block and a pumping frame. A left end of the expansion pipe and a right end of the guide pipe are in communication with each other and connected through embedding. An outer surface of the concentration block is connected with an inner surface of the expansion pipe through welding. Upper and lower ends of the pumping frame are connected with the inner surface of the expansion pipe through embedding. An outer surface of the separation block is connected with an inner surface of the expansion pipe through embedding. The concentration block is of a smooth ring structure with a semicircular cross section.

Furthermore, the separation block includes a guide block, a movable slot, a support frame and a separation ring. An outer surface of the guide block is connected with an inner surface of the expansion pipe through embedding. The movable slot is integrally formed in an inner surface of the guide block. An outer surface of the separation ring is movably connected with the inner surface of the movable slot through the support frame. The guide block is of a smooth ring structure with a trapezoidal cross section.

Furthermore, the separation ring includes an outer ring, concentration plates, a connecting column and a driven frame. An inner surface of the outer ring is connected with a bottom surface of each of the concentration plates through embedding. An outer surface of the outer ring is movably connected with the inner surface of the movable slot through the support frame. Both ends of the connecting column are connected with the inner surface of the outer ring through embedding. A center of the driven frame is movably engaged with a middle section of the connecting column. Each of the concentration plates is of a fin structure with a smooth surface. The concentration plates are provided in ten, and are evenly spaced and circularly distributed in the inner surface of the outer ring.

Furthermore, the driven frame includes a telescopic ring, pulling blocks, external pulling frames and cutting plates. The telescopic ring is movably engaged with the middle section of the connecting column. The pulling blocks are embedded in an inner surface of the telescopic ring. A bottom surface of each of the external pulling frames is connected with an outer surface of the telescopic ring through embedding. A bottom surface of each of the cutting plates is connected with a top surface of a corresponding external pulling frame through embedding. The cutting plates, the external pulling frames, and the pulling blocks are provided in four, and are evenly spaced and circularly distributed on the outer surface of the telescopic ring.

Furthermore, each of the cutting plates includes a barycenter block, a cleaning block, a dicing plate and cutting discs. A bottom surface of the barycenter block is connected with a top surface of the external pulling frame through embedding. A bottom of the cleaning plate is movably engaged with a top surface of the barycenter block. A bottom surface of the dicing plate is connected with the top surface of the barycenter block through welding. An inner surface of the dicing plate and an outer surface of the cleaning plate are in contact with each other. The cutting discs are embedded in an outer surface of the dicing plate. Each of the cutting discs is of an obtuse triangle structure with a sharpened surface.

Furthermore, the cleaning block includes a tray, a rebound plate, an impact frame and an impact ball. A bottom of the tray is movably engaged with a top surface of the barycenter block. Both ends of the rebound plate are embedded in an inner surface of the tray. A bottom surface of the impact frame is connected with a top surface of the tray through welding. An outer surface of the impact ball and a top surface of the rebound plate are in contact with each other. The impact ball is of a solid iron ball structure with a smooth surface.

BENEFICIAL EFFECTS

Compared with the prior art, the new pollutant detection equipment for environmental science in the present disclosure has the following beneficial effects.

Firstly, the water is pumped in through the pumping seat. After being sensed by the sensor head inside, the data is sent to the detection machine for analysis, and then the result is output to the data panel, so as to detect water resources. During the detection process, the water is pumped in through the water inlet pipe of the pumping pipe. After being buffered by the buffer pipe, the water makes sufficient contact with the sensor head, and then continues to be guided by the guide pipe and discharged. The water inlet pipe obtains the power of pumping through the pumping frame. The water flows onto the separation block after entering, the water is guided by the guide block at the moment and then rapidly rushes into the separation ring, and the impact force is absorbed by the support frame. The water is concentrated towards the center through the concentration plates after entering, and the driven frame is driven to rotates by the water. If there is a lot of root systems of duckweed in the water, after the water enters, the root systems of duckweed can be concentrated through the concentration plates and cut up through the driven frame, and then the root systems of duckweed continue to move backwards and are cut for the second time, so that the root systems are cut into fine and small segments, the phenomenon that the root systems are entangled in the pumping frame so as to enable the pumping frame to be jammed is avoided, and the accuracy of the detection result is guaranteed.

Secondly, when the driven frame is impacted by water, the cutting plates arranged on the outer surface of the telescopic ring can produce thrust for rotation due to the flow of the water, causing the telescopic ring rotates and expands outward through centrifugal force. The pulling blocks are stretched, and the diameter is increased. Moreover, the external pulling frames are stretched through centrifugal force, and the coverage area of the cutting plates is increased. At this time, the cutting plates will rotate rapidly along with the rotation of the telescopic ring, so that the dicing plates arranged on the top of the cutting plates dice quickly in the water. The cutting discs arranged on the surface of the dicing plates also make contact with the root systems of duckweed involved in the water. By combining the kinetic energy of rotation with the sharpened surface, the kinetic energy is concentrated, so that the roots are cut quickly. At the same time, the centrifugal force produced by rotation will be applied to the cleaning blocks, the impact balls arranged on the rebound plates quickly move outward and impacts the impact frames, so that the impact frames vibration and output the vibration to the dicing plates. Thus, the dicing plates vibration, and cooperate with the cutting discs to further enhance the cutting effect. Moreover, the root systems are avoided from being attached, the size of the systems is further reduced, the probability of entanglement is reduced. Meanwhile, the cut root systems can be discharged smoothly to avoid blockage.

Figure 1:
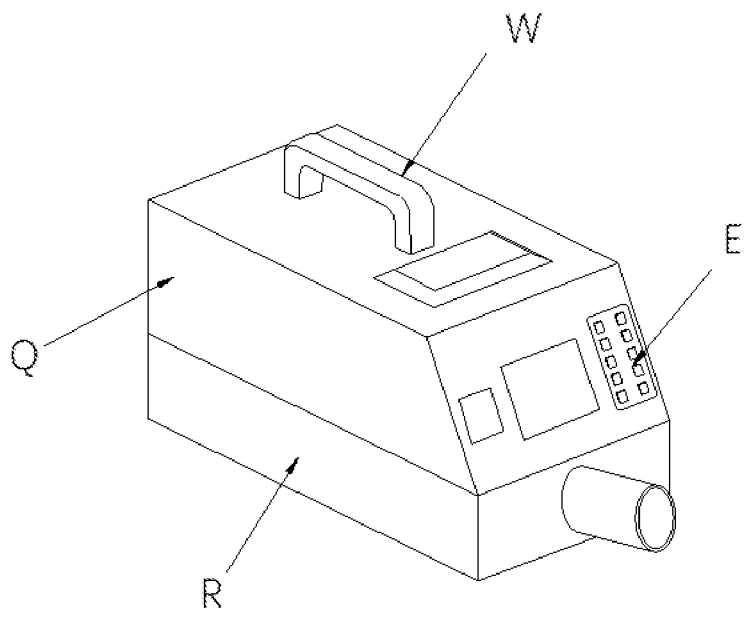
FIG. 1 is a stereoscopic structural schematic diagram of a new pollutant detection equipment for environmental science in the present disclosure.
Figure 2:
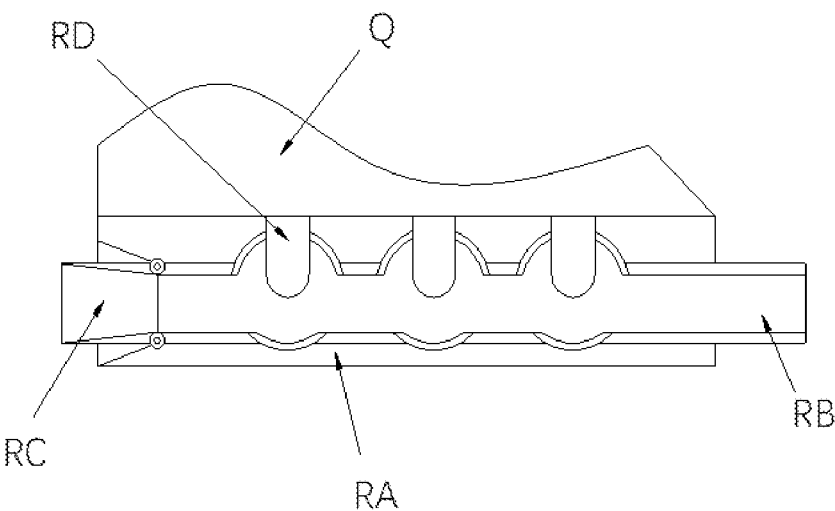
FIG. 2 is a structural schematic diagram of a front cross section of a pumping seat in the present disclosure.
Figure 3:
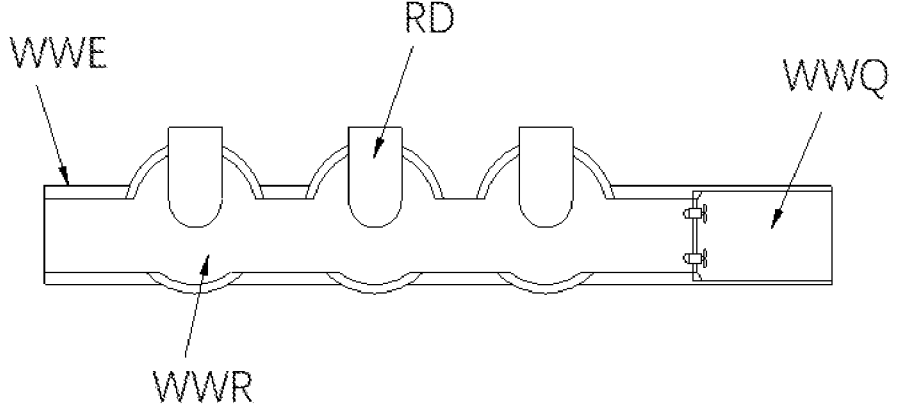
FIG. 3 is a structural schematic diagram of a front cross section of a pumping pipe in the present disclosure.
Figure 4:
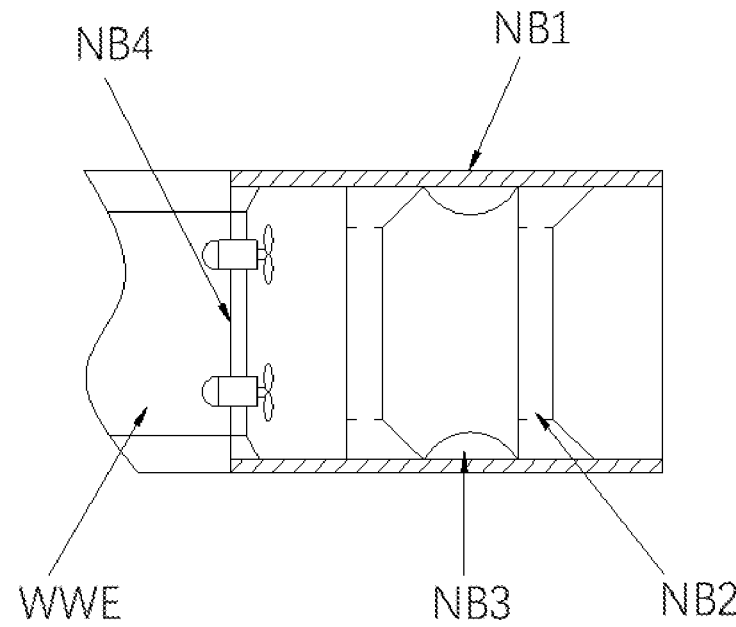
FIG. 4 is a structural schematic diagram of a front cross section of a water inlet pipe in the present disclosure.
Figure 5:
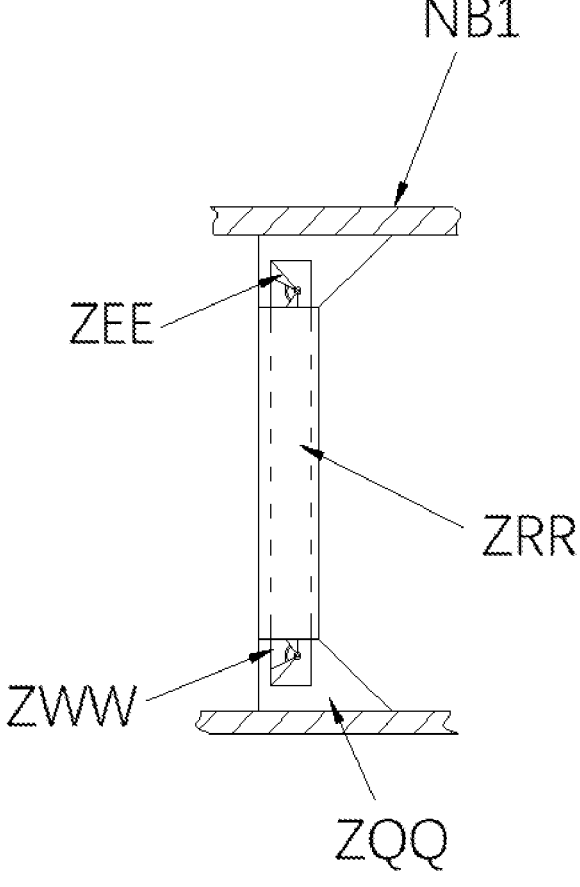
FIG. 5 is a structural schematic diagram of a front cross section of a separation block in the present disclosure.
Figure 6:
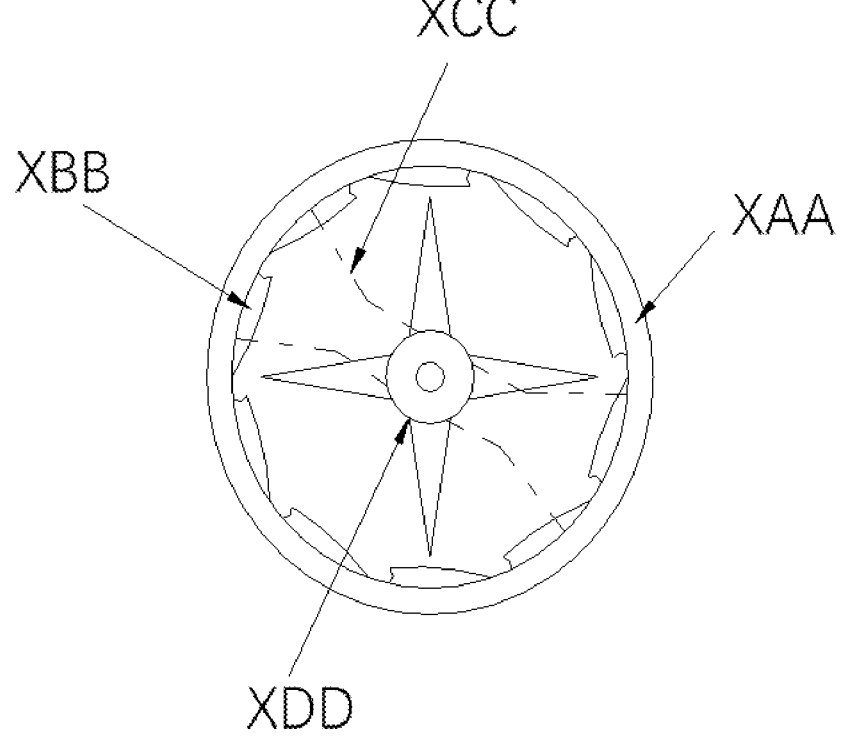
FIG. 6 is a structural schematic diagram of a right cross section of a separation ring in the present disclosure.

Reference signs: Q, detection machine; W, carrying handle; E, data panel; R, pumping seat; RA, connecting block; RB, pumping pipe; RC, discharge pipe; RD, sensor head; WWQ, water inlet pipe; WWE, guide pipe; WWR, buffer pipe; NB1, expansion pipe; NB2, separation block; NB3, concentration block; NB4, pumping frame; ZQQ, guide block; ZWW, movable slot; ZEE, support frame; ZRR, separation ring; XAA, outer ring; XBB, concentration plate; XCC, connecting column; XDD, driven frame; AMD, telescopic ring; BMD, pulling block; CMD, external pulling frame; DMD, cutting plate; LL1, barycenter block; LL2, cleaning block; LL3, dicing plate; LL4, cutting disc; GGA, tray; GGB, rebound plate; GGC, impact frame; and GGD, impact ball.

DETAILED DESCRIPTION OF THE EMBODIMENTS

The following clearly and completely describes the technical solution in the present disclosure with reference to the attached figures. Apparently, the described embodiments are a part rather than all of the embodiments of the present disclosure. All other embodiments obtained by those skilled in the art based on the embodiments of the present disclosure without creative efforts shall fall within the protection scope of the present disclosure.

In the description of the present disclosure, it needs to be illustrated that the indicative direction or position relations of the terms such as "center", "top", "bottom", "left", "right", "vertical", "horizontal", "inside" and "outside" are direction or position relations illustrated based on the attached figures, just for facilitating the description of the present disclosure and simplifying the description, but not for indicating or hinting that the indicated device or element must be in a specific direction and is constructed and operated in the specific direction, the terms cannot be understood as the restriction of the present disclosure. Moreover, the terms such as "first", "second" and "third" are just used for distinguishing the description, but cannot be understood to indicate or hint relative importance.

Embodiment I

Referring to FIG. 1 to FIG. 6, an embodiment of the new pollutant detection equipment for environmental science in the present disclosure is as follows. A new pollutant detection equipment for environmental science structurally includes a detection machine Q, a carrying handle W, a data panel E and a pumping seat R. A top surface of the detection machine Q is connected with a bottom surface of the carrying handle W through welding. A top surface of the pumping seat R is connected with a bottom surface of the detection machine Q through embedding. The data panel E is embedded in a right side of the detection machine Q. The pumping seat R includes a connecting block RA, a pumping pipe RB, a discharge pipe RC and sensor heads RD. A top surface of the connecting block RA is connected with the bottom surface of the detection machine Q through embedding. The pumping pipe RB is embedded in an interior of the connecting block RA. A right end of the discharge pipe RC and a left end of the pumping pipe RB are in communication with each other and movably engaged. Each of the sensor heads RD is embedded in a top surface of the pumping pipe RB. The discharge pipe RC is a tubular structure including two plates with a triangular cross section, and the two plates are pivotably connected to upper and lower portions of the left end of the discharge pipe RC through a hinge shaft, so that the two plates rotate around the hinge shaft to expand the left end of the discharge pipe RC to increase the water output when the water flow pressure is too high, and then the internal pressure of the pumping pipe RB is reduced.

The pumping pipe RB includes a water inlet pipe WWQ, a guide pipe WWE and buffer pipes WWR. A left end of the water inlet pipe WWQ and a right end of the guide pipe WWE are in communication with each other and connected through embedding. Both ends of the buffer pipe WWR and a middle section of the guide pipe WWE are in communication with each other and connected through electric welding. Each of the sensor heads RD are embedded in a top surface of the buffer pipe WWR. The buffer pipe WWR is of a spherical tube structure with a smooth inner wall, which is beneficial for causing eddy currents in the incoming water, reducing the flow rate, and allowing for more sufficient contact between the water and the sensor head RD.

The water inlet pipe WWQ includes an expansion pipe NB1, a separation block NB2, a concentration block NB3 and a pumping frame NB4. A left end of the expansion pipe NB1 and a right end of the guide pipe WWE are in communication with each other and connected through embedding. An outer surface of the concentration block NB3 is connected with an inner surface of the expansion pipe NB1 through welding. Upper and lower ends of the pumping frame NB4 are connected with the inner surface of the expansion pipe NB1. An outer surface of the separation block NB2 is connected with the inner surface of the expansion pipe NB1 through embedding. The concentration block NB3 is of a smooth ring structure with a semicircular cross section, which is beneficial for raising the incoming water and thus entering a center of the separation block NB2 at a higher angle.

The separation block NB2 includes a guide block ZQQ, a movable slot ZWW, a support frame ZEE and a separation ring ZRR. An outer surface of the guide block ZQQ is connected with an inner surface of the expansion pipe NB1 through embedding. The movable slot ZWW is integrally formed in an inner surface of the guide block ZQQ. An outer surface of the separation ring ZRR is movably connected with an inner surface of the movable slot ZWW through the support frame ZEE. The guide block ZQQ is of a smooth ring structure with a trapezoidal cross section, which is beneficial for raising and guiding the water, and reducing the flow resistance of the water.

The separation ring ZRR includes an outer ring XAA, concentration plates XBB, a connecting column XCC and a driven frame XDD. An inner surface of the outer ring XAA is connected with a bottom surface of each of the concentration plates XBB through embedding. An outer surface of the outer ring XAA is movably connected with the inner surface of the movable slot ZWW through the support frame ZEE. Both ends of the connecting column XCC are connected with the inner surface of the outer ring XAA through embedding. A center of the driven frame XDD is movably engaged with a middle section of the connecting column XCC. Each of the concentration plates XBB is of a fin structure with a smooth surface. The concentration plates XBB are provided in ten, and are evenly spaced and circularly distributed on the inner surface of the outer ring XAA, which is beneficial for concentrating the water towards the center to better impact the driven frame XDD.

Based on the above embodiment, the working principle of the new pollutant detection equipment for environmental science in the present disclosure is as follows. The water is pumped in through the pumping seat R. After being sensed by the sensor head RD inside, the data is sent to the detection machine Q for analysis, and then the result is output to the data panel E, so as to detect water resources. During the detection process, the water is pumped in through the water inlet pipe WWQ of the pumping pipe RB. After being buffered by the buffer pipe WWR, the water makes sufficient contact with the sensor head RD, and then continues to be guided by the guide pipe WWE and discharged. The water inlet pipe WWQ obtains the power of pumping through the pumping frame NB4. The water flows onto the separation block NB2 after entering, the water is guided by the guide block ZQQ at the moment and then rapidly rushes into the separation ring ZRR, and the impact force is absorbed by the support frame ZEE. The water is concentrated towards the center through the concentration plates XBB after entering, and the driven frame XDD is driven to rotate by the water. If there is a lot of root systems of duckweed in the water, after the water enters, the root systems of duckweed can be concentrated through the concentration plates XBB and cut up through the driven frame XDD, and then the root systems of duckweed continue to move backwards and are cut for a second time, so that the root systems are cut into fine and small segments, the phenomenon that the root systems are entangled in the pumping frame NB4 so as to enable the pumping frame to be jammed is avoided, and the accuracy of the detection result is guaranteed.

Embodiment II

Figure 7:
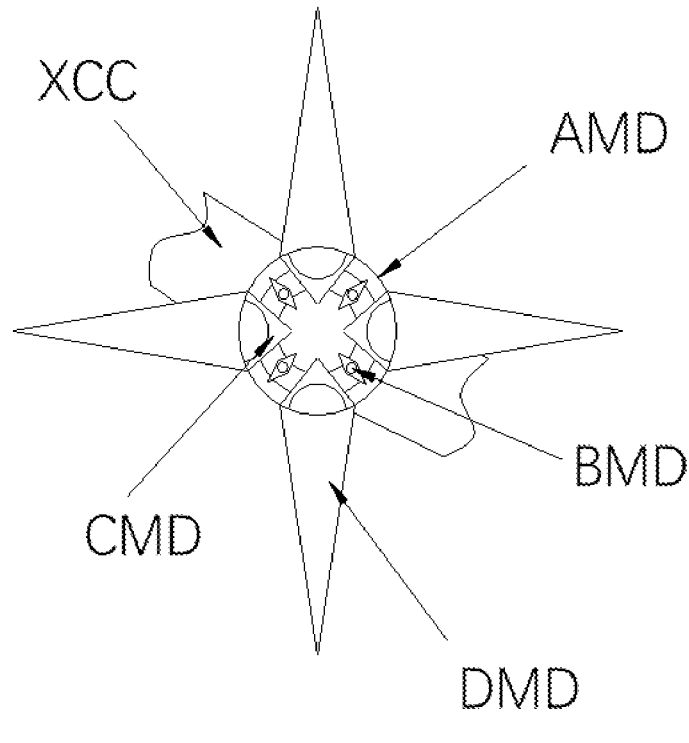
FIG. 7 is a structural schematic diagram of a front cross section of a driven frame in the present disclosure.
Figure 8:
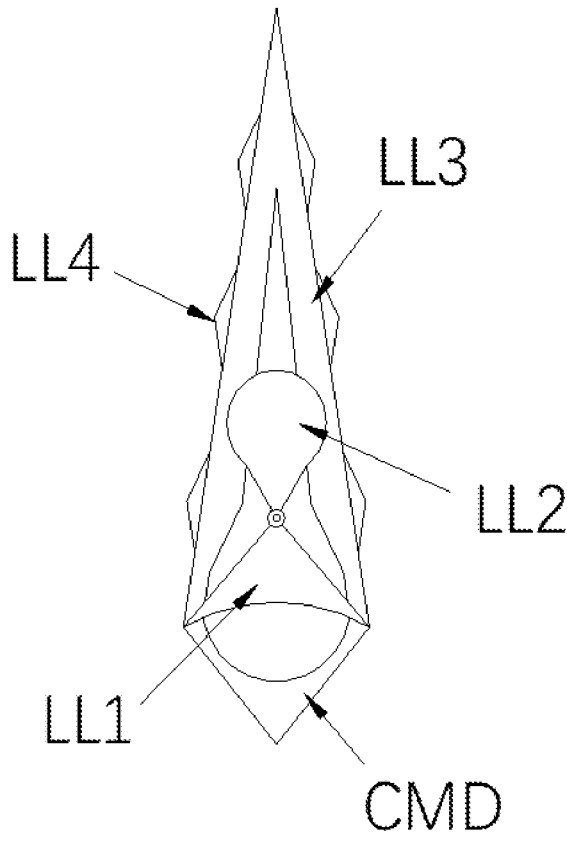
FIG. 8 is a structural schematic diagram of a front cross section of a cutting disc in the present disclosure.
Figure 9:
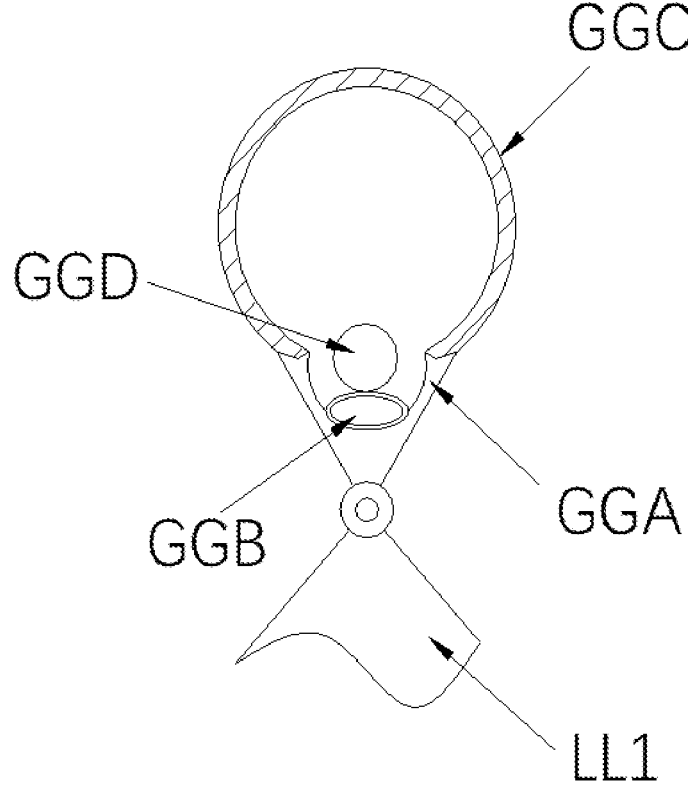
FIG. 9 is a structural schematic diagram of a front cross section of a cleaning block in the present disclosure.

Referring to FIG. 7 to FIG. 9, an embodiment of the new pollutant detection equipment for environmental science in the present disclosure is as follows. The driven frame XDD includes a telescopic ring AMD, pulling blocks BMD, external pulling frames CMD and cutting plates DMD. The telescopic ring AMD is movably engaged with the middle section of the connecting column XCC. The pulling blocks BMD are embedded in an inner surface of the telescopic ring AMD. A bottom surface of each of the external pulling frames CMD is connected with an outer surface of the telescopic ring AMD through embedding. A bottom surface of each of the cutting plates DMD is connected with a top surface of a corresponding external pulling frame CMD through embedding. The cutting plates DMD, the external pulling frames CMD, and the pulling blocks BMD are provided in four, and are evenly spaced and circularly distributed on the outer surface of the telescopic ring AMD, which is beneficial for increasing the cutting frequency, and thus cutting the incoming root systems into smaller segments.

Wherein, each of the cutting plates includes a barycenter block LL1, a cleaning block LL2, a dicing plate LL3 and cutting discs LL4. A bottom surface of the barycenter block LL1 is connected with a top surface of the external pulling frame CMD through embedding. A bottom of the cleaning plate LL2 is movably engaged with a top surface of the barycenter block LL1. A bottom surface of the dicing plate LL3 is connected with a top surface of the barycenter block LL1 through welding. An inner surface of the dicing plate LL3 and an outer surface of the cleaning plate LL2 are in contact with each other. The cutting discs LL4 are embedded in an outer surface of the dicing plate LL3. Each of the cutting discs LL4 is of an obtuse triangle structure with a sharpened surface, which is beneficial for causing the greater pressure on the contact surface, and allowing the roots to be cut off more quickly.

The cleaning block LL2 includes a tray GGA, a rebound plate GGB, an impact frame GGC and an impact ball GGD. A bottom of the tray GGA is movably engaged with a top surface of the barycenter block LL1. Both ends of the rebound plate GGB is embedded in an inner surface of the tray GGA. A bottom surface of the impact frame GGC is connected with a top surface of the tray GGA through welding. An outer surface of the impact ball GGD and a top surface of the rebound plate GGB are in contact with each other. The impact ball GGD is of a solid iron ball structure with a smooth surface, which is beneficial for reducing the resistance to movement, and causing the greater kinetic energy impact force.

Based on the above embodiments, the working principle of the new pollutant detection equipment for environmental science in the present disclosure is as follows. When the driven frame XDD is impacted by the water, the cutting plates DMD arranged on the outer surface of the telescopic ring AMD can produce thrust for rotation due to the flow of the water, causing the telescopic ring AMD to rotate and expand outward through centrifugal force. The pulling blocks BMD are stretched, and the diameter is increased. Moreover, the external pulling frames CMD are stretched through centrifugal force, and the coverage area of the cutting plates DMD is increased. At this time, the cutting plates DMD will rotate rapidly along with the rotation of the telescopic ring AMD, so that the dicing plates LL3 arranged on the top of the cutting plates dice quickly in the water. The cutting discs LL4 arranged on the surface of the dicing plates also make contact with the root systems of duckweed involved in the water. By combining the kinetic energy of rotation with the sharpened surface, the kinetic energy is concentrated, so that the roots are cut quickly. At the same time, the centrifugal force produced by rotation will be applied to the cleaning blocks LL2, the impact balls GGD arranged on the rebound plates GGB quickly move outward and impact the impact frames GGC, so that the impact frames GGC vibrations and output the vibration to the dicing plates LL3. Thus, the dicing plates LL3 vibrations, and cooperate with the cutting discs LL4 to further enhance the cutting effect. Moreover, the root systems are avoided from being attached, the size of the root systems is further reduced, the probability of entanglement is reduced. Meanwhile, the cut root systems can be discharged smoothly to avoid blockage.

The technical features of the above-mentioned embodiments may be arbitrarily combined, and all possible combinations of the technical features in the above-mentioned embodiments are not described for simplicity of description. However, as long as the combinations of the technical features do not contradict one another, the technical features should be considered to fall within the scope of the description of the present disclosure.

Therefore, for every point, the embodiments should be regarded as exemplary embodiments and are unlimited, the scope of the present disclosure is limited by the claims appended hereto, and therefore, all changes, including the meanings and scopes of equivalent elements, of the claims are aimed to be included in the present disclosure. Any mark of attached figures in the claims should not be regarded as limitation to the involved claims.

What is claimed is:

1. A new pollutant detection equipment for environmental science, comprising a detection machine (Q), a carrying handle (W), a data panel (E) and a pumping seat (R), wherein a top surface of the detection machine (Q) is connected with a bottom surface of the carrying handle (W) through welding, a top surface of the pumping seat (R) is connected with a bottom surface of the detection machine (Q) through embedding, and the data panel (E) is embedded in a right side of the detection machine (Q);

the pumping seat (R) comprises a connecting block (RA), a pumping pipe (RB), a discharge pipe (RC) and sensor heads (RD), a top surface of the connecting block (RA) is connected with the bottom surface of the detection machine (Q) through embedding, the pumping pipe (RB) is embedded in an interior of the connecting block (RA), a right end of the discharge pipe (RC) and a left end of the pumping pipe (RB) are in communication with each other and movably engaged, and each of the sensor heads (RD) are embedded in a top surface of the pumping pipe (RB).

2. The new pollutant detection equipment for environmental science according to claim 1, wherein the pumping pipe (RB) comprises a water inlet pipe (WWQ), a guide pipe (WWE) and buffer pipes (WWR), a left end of the water inlet pipe (WWQ) and a right end of the guide pipe (WWE) are in communication with each other and connected through embedding, both ends of each of the buffer pipes (WWR) and a middle section of the guide pipe (WWE) are connected with each other and connected through electric welding, and each of the sensor heads (RD) is embedded in a top surface of the buffer pipe (WWR).

3. The new pollutant detection equipment for environmental science according to claim 2, wherein the water inlet pipe (WWQ) comprises an expansion pipe (NB1), a separation block (NB2), a concentration block (NB3) and a pumping frame (NB4), a left end of the expansion pipe (NB1) and a right end of the guide pipe (WWE) are in communication with each other and connected through embedding, an outer surface of the concentration block (NB3) is connected with an inner surface of the expansion pipe (NB1) through welding, upper and lower ends of the pumping frame (NB4) are connected with the inner surface of the expansion pipe (NB1) through embedding, and an outer surface of the separation block (NB2) is connected with the inner surface of the expansion pipe (NB1) through embedding.

4. The new pollutant detection equipment for environmental science according to claim 3, wherein the separation block (NB2) comprises a guide block (ZQQ), a movable slot (ZWW), a support frame (ZEE) and a separation ring (ZRR), an outer surface of the guide block (ZQQ) is connected with the inner surface of the expansion pipe (NB1) through embedding, the movable slot (ZWW) is integrally formed in an inner surface of the guide block (ZQQ), and an outer surface of the separation ring (ZRR) is movably connected with an inner surface of the movable slot (ZWW) through the support frame (ZEE).

5. The new pollutant detection equipment for environmental science according to claim 4, wherein the separation ring (ZRR) comprises an outer ring (XAA), concentration plates (XBB), a connecting column (XCC) and a driven frame (XDD), an inner surface of the outer ring (XAA) is connected with a bottom surface of each of the concentration plates (XBB) through embedding, an outer surface of the outer ring (XAA) is movably connected with the inner surface of the movable slot (ZWW) through the support frame (ZEE), both ends of the connecting column (XCC) are connected with the inner surface of the outer ring (XAA) through embedding, and a center of the driven frame (XDD) is movably engaged with a middle section of the connecting column (XCC).

6. The new pollutant detection equipment for environmental science according to claim 5, wherein the driven frame (XDD) comprises a telescopic ring (AMD), pulling blocks (BMD), external pulling frames (CMD) and cutting plates (DMD), the telescopic ring (AMD) is movably engaged with the middle section of the connecting column (XCC), the pulling blocks (BMD) are embedded in an inner surface of the telescopic ring (AMD), a bottom surface of each of the external pulling frames (CMD) is connected with an outer surface of the telescopic ring (AMD) through embedding, and a bottom surface of each of the cutting plates (DMD) is connected with a top surface of a corresponding external pulling frame (CMD) through embedding.

7. The new pollutant detection equipment for environmental science according to claim 6, wherein each of the cutting plates (DMD) comprises a barycenter block (LL1), a cleaning block (LL2), a dicing plate (LL3) and cutting discs (LL4), a bottom surface of the barycenter block (LL1) is connected with a top surface of the external pulling frame (CMD) through embedding, a bottom of the cleaning plate (LL2) is movably engaged with a top surface of the barycenter block (LL1), a bottom surface of the dicing plate (LL3) is connected with the top surface of the barycenter block (LL1) through welding, an inner surface of the dicing plate (LL3) and an outer surface of the cleaning plate (LL2) are in contact with each other, and the cutting discs (LL4) are embedded in an outer surface of the dicing plate (LL3).

8. The new pollutant detection equipment for environmental science according to claim 7, wherein the cleaning block (LL2) comprises a tray (GGA), a rebound plate (GGB), an impact frame (GGC) and an impact ball (GGD), a bottom of the tray (GGA) is movably engaged with a top surface of the barycenter block (LL1), both ends of the rebound plate (GGB) are embedded in an inner surface of the tray (GGA), a bottom surface of the impact frame (GGC) is connected with a top surface of the tray (GGA) through welding, and an outer surface of the impact ball (GGD) and a top surface of the rebound plate (GGB) are in contact with each other.

* * * * *